United States Patent
Cantor

(10) Patent No.: US 7,165,973 B2
(45) Date of Patent: Jan. 23, 2007

(54) METHOD FOR NON-VERBAL ASSESSMENT OF HUMAN COMPETENCE

(76) Inventor: Michael B. Cantor, 538 Burlington Rd., Suite B, Atlanta, GA (US) 30307

( * ) Notice: Subject to any disclaimer, the term of this patent is extended or adjusted under 35 U.S.C. 154(b) by 451 days.

(21) Appl. No.: 10/333,596

(22) PCT Filed: Sep. 21, 2001

(86) PCT No.: PCT/US01/29665

§ 371 (c)(1),
(2), (4) Date: Jan. 21, 2003

(87) PCT Pub. No.: WO02/25855

PCT Pub. Date: Mar. 28, 2002

(65) Prior Publication Data

US 2004/0002046 A1    Jan. 1, 2004

Related U.S. Application Data

(60) Provisional application No. 60/234,463, filed on Sep. 21, 2000.

(51) Int. Cl.
*G09B 3/00* (2006.01)
*G09B 7/00* (2006.01)

(52) U.S. Cl. .................... 434/322; 434/219; 434/327

(58) Field of Classification Search ............. 434/64, 434/65, 118, 219, 305, 307 R, 322, 327, 362, 434/365; 463/4; 701/301; 706/12; 709/216; 345/473; 342/451; 378/88, 98.7; 356/237.5, 356/446; 351/209; 367/127; 73/1.82; 718/103; 349/65; 430/30

See application file for complete search history.

(56) References Cited

U.S. PATENT DOCUMENTS

| | | | | |
|---|---|---|---|---|
| 4,533,918 A | * | 8/1985 | Virnot | 342/451 |
| 5,253,283 A | * | 10/1993 | Annis et al. | 378/98.7 |
| 5,479,252 A | * | 12/1995 | Worster et al. | 356/237.5 |
| 5,544,267 A | | 8/1996 | Mahoney et al. | |
| 5,568,209 A | | 10/1996 | Priester et al. | |
| 5,574,212 A | * | 11/1996 | Madsen et al. | 73/1.82 |
| 5,687,291 A | | 11/1997 | Smyth | |
| 5,822,584 A | * | 10/1998 | Thompson et al. | 718/103 |
| 5,963,280 A | * | 10/1999 | Okuda et al. | 349/65 |
| 5,981,119 A | * | 11/1999 | Adams | 430/30 |
| 6,065,046 A | * | 5/2000 | Feinberg et al. | 709/216 |
| 6,082,545 A | | 7/2000 | Ford et al. | |
| 6,164,975 A | | 12/2000 | Weingarden et al. | |
| 6,178,141 B1 | * | 1/2001 | Duckworth et al. | 367/127 |
| 6,353,814 B1 | * | 3/2002 | Weng | 706/12 |
| 6,431,982 B1 | * | 8/2002 | Kobayashi | 463/4 |
| 6,438,491 B1 | * | 8/2002 | Farmer | 701/301 |
| 6,459,764 B1 | * | 10/2002 | Chalmers et al. | 378/88 |

(Continued)

*Primary Examiner*—Joe H. Cheng
(74) *Attorney, Agent, or Firm*—Laurence P. Colton; Powell Goldstein LLP

(57) ABSTRACT

A method of testing a subject's competence for operating machines by successively presenting a plurality of pages of scattered images to the subject, having the subject establish a path through the scattered images on each of the plurality of pages, recording the absolute time required for the subject to establish the path through the scattered images on each of the plurality of pages, determining the relative time required for the subject to establish the path on at least two of the plurality of pages of scattered images, and classifying the subjects competence for operating machines based on the absolute time and the relative time.

51 Claims, 11 Drawing Sheets

U.S. PATENT DOCUMENTS 6,664,965 B1 * 12/2003 Yamamoto et al. ......... 345/473
6,795,195 B1 * 9/2004 Barbour et al. ............. 356/446
6,916,096 B1 * 7/2005 Eberl et al. ................. 351/209

* cited by examiner

METHOD FOR NON-VERBAL ASSESSMENT OF HUMAN COMPETENCE

STATEMENT OF RELATED APPLICATIONS

This patent application claims priority on United States of America Provisional Patent Application No. 60/234,463 filed on Sep. 21, 2000.

BACKGROUND OF THE INVENTION

1. Technical Field

The present invention relates generally to the field of assessing human competence and more specifically to assessing human competence on man-made machines using non-verbal testing methods.

2. Prior Art

The best-known test of driver competence is the Useful Field of View (UFOV) test that recently has been implemented on a personal computer. Ball, K. and Owsley, C., Identifying correlates of accident involvement for the older driver, *Human Factors,* 33(5), 583–595. The basic task has the subject indicate the presence or absence of a stimulus in a visual field that can include a silhouette of a car or truck. The duration and/or intensity of the stimulus is manipulated so as to determine a detection threshold value. In validation trials, almost exclusively with elderly drivers, the threshold has been shown to be significantly correlated with the probability of a collision.

The present invention differs significantly from UFOV on two key points. First, the present invention uses absolute and relative response rate rather than stimulus threshold as the primary dependent variable. Second, the present invention's key measure of competence, a favorable interaction between channel capacity (CC) and situational awareness (SA), is taken throughout the range of CC. Since CC is correlated with age, fine distinctions in crash proneness can be determined at all age levels. UFOV measures a minimal necessary threshold for crash avoidance, which may indeed be workable for assessing older drivers. Indeed, UFOV has been exclusively validated on elderly drivers. Importantly, one would not expect that UFOV would make fine distinctions in crash proneness among younger drivers who have much faster response speed than the elderly.

Trails B is a public domain test that was originally part of the Army Individual Test Battery (1944) and later a standard component of the popular Halstead-Reitan Neuropsychological Test Battery (Halstead, 1947; Reitan & Davison, 1974). The Trails B test is still commonly used for the diagnosis of certain types of neuropathology and has been shown to predict crash proneness in a motor vehicle. Computer-based versions of the Trails B have been tested, especially for the evaluation of older drivers.

The present invention differs from Trails B in four fundamental ways. First, the adult Trails B has 25 letters and numbers whereas the present invention has 15. The choice of 15 letters and numbers adds to the sensitivity of the present invention and was empirically determined. Fewer than 15 such points is too low a workload, creating a ceiling effect in response speed among subjects. More than 15 points per page creates a floor effect among subjects. Second, Trails B is a single page of letters and numbers whereas the present invention includes four pages, the last of which has interspersed distracting pictures. Third, Trails B subjects are coached one-on-one through the making of the trail (and are required to correct errors and omissions) whereas the present invention has subjects read the instructions and then commence unassisted. Fourth, the key datum for Trails B is simply the time to complete the full (corrected) trait; there is no measure of the person's response variability. The present invention, on the other hand, includes the number of letters and numbers traversed per second (speed) on each of the four pages. This allows a measure of both absolute response speed and variability among pages.

CogScreen is an aviation related computer-administered and scored cognitive-screening instrument designed to assess deficits or changes in attention, immediate- and short-term memory, visual perceptual functions, sequencing functions, logical problem solving, calculation skills, reaction time, simultaneous information processing abilities, and executive functions. CogScreen has 95 scales, takes 45 minutes to an hour to administer, and lacks the sensitivity of the present invention (especially in the upper reaches of ability where pilots are over-represented).

Thus it can be seen that there exists a need for a valid, simple-to-administer, flexible, brief, assessment test for determining the ability of humans to operate man-made machines. It is to this need that the present invention is directed.

BRIEF SUMMARY OF THE INVENTION

The present invention is a non-verbal assessment test that is available as a paper/pencil version, as a computer-based program, and as an Internet or intranet application. The test can include a form for the person's name and other bibliographic information, instructions and a sample of the assessment task. The sample consists of a page of numbers from 1 to 5 and letters from A to E scattered randomly about the page, with the "1" in the middle. The actual test comprises four pages of 15 numbers and letters (the numbers from 1 to 8 and the letters from A to G) randomly scattered about each page. The fourth page of the actual test further comprises small images that are neither numbers nor letters interspersed among the numbers and letters.

The basic task is to make a continuous path, starting at "1" and switching from number to letter, keeping numbers and letters in order (1, A, 2, B, etc.). The actual test comprises the four pages previously mentioned, and can further comprise two additional pages that comprise 12 letters and numbers, with the second additional page also comprising small pictures interspersed among the numbers and letters. The subject completes the basic task on all of the pages presented to the subject. For the paper/pencil version, the individual is told to draw the line among the letters and numbers as fast as possible without making mistakes and to keep going if a mistake is made. For the computer-based version, the individual is told to click (using a mouse or other entry device) on the numbers and letters in the alternating order previously mentioned.

The test is scored on the basis of channel capacity (CC) and situational awareness (SA). CC refers to baud rate or bandwidth and is the throughput of a system or, more quantitatively, the amount of information (in bits) that a person can process (as indicated by a response) per unit of time. More specifically, CC is the absolute time it takes the subject to complete each page. The CC then is compared to the SA, which is the relative speed of completing one test page to another test page. At each level of CC, SA can either aggravat or mitigate the incidence of preventable collisions. Operationally, SA is quantified by five relative response rates, i.e. ratios of speed between pages. At each level of CC, a pair of SA values optimally predicts crash frequency.

Every operational job has an information-processing requirement. Driving a slow-moving transit bus, for instance, demands less of an operator than piloting an airliner. Whatever the job, a mismatch between the demands of the job and the abilities of the operator is a recipe for disaster—for the individual, for the company and for the innocent victims. The invention assesses crash proneness by measuring two key abilities—channel capacity and situational awareness. Channel capacity is the person's speed of information processing or throughput; it is the same concept as "baud rate", the speed at which modems send and receive data. Situational awareness is the tendency to be vigilant in the face of surprise and boredom; it is similar to the concept of big picture in driving or court sense in basketball.

The invention can help identify the 20% of drivers who have about 60% of the preventable collisions. Among the many applications of the invention are the assessment of fleet drivers, aging drivers, and teenagers. Fleet operators can reduce preventable collisions by about 25% when they use the invention for pre-employment screening. The invention can provide an objective assessment of an elderly driver's risk and helps make an intelligent decision about this very important issue. Teenagers are 7% of the population, yet they have 14% of the fatalities and 20% of the collisions. The invention can help parents of new drivers assess their child's risk and how to deal with it.

One feature of the present invention is a method for testing a subject's competence to operate a machine based on a simple short test.

Another feature of the present invention is a method for testing a subject's ability to control a motor vehicle, and the likelihood a subject will be involved in or cause a motor vehicle accident.

Still another feature of the present invention is a method for testing a subject's ability to perform certain job functions, including repetitive functions and emergency situation functions.

These features, and other features, objects and advantages of the present invention will become more apparent to those of ordinary skill in the art when the following detailed description of the preferred embodiments is read in conjunction with the appended drawings and appendix.

DETAILED DESCRIPTION OF THE PREFERRED EMBODIMENTS

Figure 1:
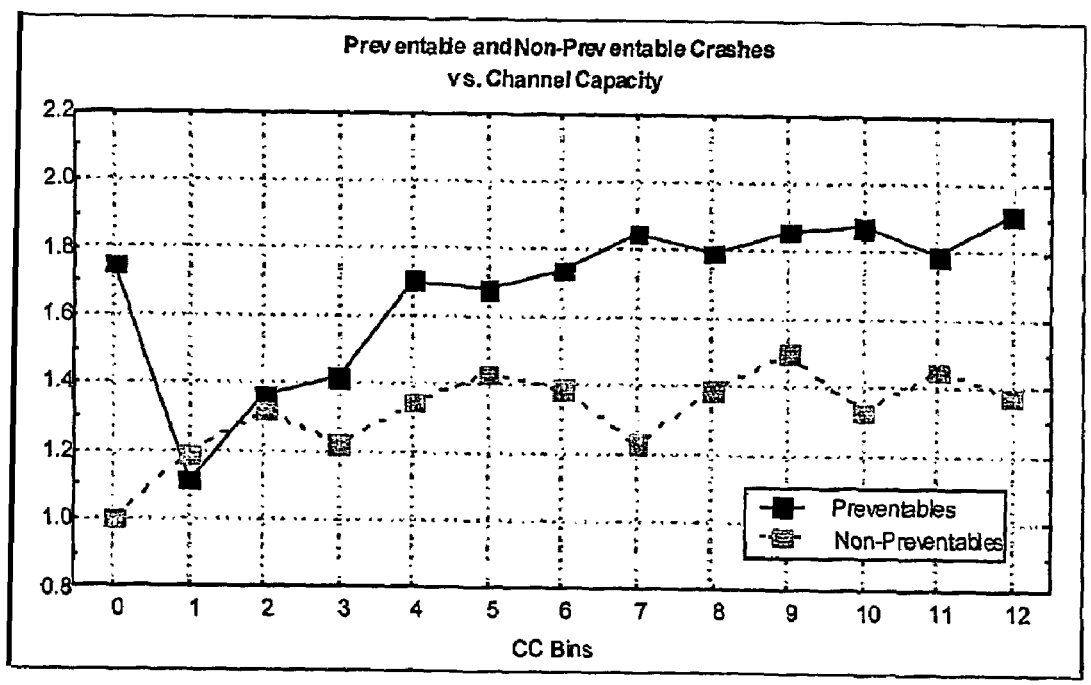
FIG. 1 is a graph of lifetime crash frequency corrected for a person's age.

The present invention is a non-verbal test for the assessment of human competence in a man-machine system. Competence includes but is not limited to the safe driving of cars, buses, trucks and other motor vehicles; the piloting of aircraft; the operational control of pipelines, power lines and systems, telephone lines and systems, and railroads; the driving of trains, ships and military vehicles; and the dispensing of drugs by pharmacists, among many other real-time, operational tasks.

Each of these tasks (occupations) makes certain information processing demands on the operator. A transit bus, for example, operating at low speed over a familiar route with many stops makes relatively low information processing demands (in bits/sec) on the operator. A car or a long-haul truck traveling at fairly high speed on a rural road, on the other hand, is associated with a much higher workload for the operator. Likewise, an airliner flying in IFR conditions with an engine out, high cross winds and a blown tire requires still greater levels of information processing.

To avert disasters, the information processing capacity of the operator must match the peak demands of the system (in bits/sec). In one embodiment, the present invention measures the information processing profile of an operator and, once validated against key criterion measures, e.g. crash frequency in an automobile, truck, or other vehicle, assesses his or her risk of having preventable and non-preventable incidents. In another embodiment, the present invention measures the information processing of other professionals, such as pilots, pipeline operators and pharmacists. However, the invention is not limited to these professions or occupations, but is applicable to many professions and occupations in which decision-making and/or multi-tasking is required.

The test measures a person's absolute speed, channel capacity CC, in negotiating an attention-switching task whose information processing demands are equal to an average operational task, e.g. driving. In addition to absolute speed, this test uniquely measures relative speed, that is, situational awareness, SA. CC and SA are both necessary and sufficient for predicting operational competence. Because the parameters of the test have been optimized empirically, the present invention test is "fat-free." There are no face-valid components that "ought to work" and are "probably needed" as is the case with other computer-based tests.

The test is a "does it match?" type of test. In other words, this invention, for the most part, is not a "more is better" type of test. That is, a person is not a safer driver the higher his CC. Test data show that there are safe drivers at both the very highest and very lowest levels of CC. At every level of CC, there are values of SA associated with safe driving and there are some that are not.

CC, as measured by this test, is correlated with a person's work speed. For example, in a simulation of the pharmacist's job, it has been found that CC is correlated with prescriptions filled per hour. CC also is correlated with a person's speed in negotiating an obstacle course in an automobile. It appears that people adjust their driving speed to match their CC, i.e. they titrate their speed to their CC, thereby holding risk in homeostasis. This helps to explain why teenagers, with peak CC at age 17, get more than their share of speeding tickets and have proportionally more over-speed collisions. The elderly, on the other hand, with the lowest CC, are under-represented in speeding tickets. CC on the test is the empirical basis for comments about driving speed, following too closely, etc. in the assessment report created by the test.

Speed on a task, including driving speed, is not linear with respect to CC. As CC increases, task speed increases overall but follows a saw-tooth function. In particular, task speed is higher than would be expected at CC-2, CC-4, and CC-6. This is viewed as a neither "fish nor fowl" phenomenon. All CC-1 drivers are low risk, presumably because they drive slowly with respect to the average demands of traffic. It appears that the CC-2 profile is over-represented with high-risk drivers because they process information faster than CC-1 drivers and consequently driver faster than CC-1. On the other hand, CC-2 drivers do not process as fast as the CC-3 drivers. So, CC-2 drivers will not do what the CC-1 drivers do (drive slowly) and cannot do what the CC-3 drivers do (process faster). The CC-2 drivers are classified neither as "fish nor as fowl," but are classified as on the edge. CC-2 drivers have less spare capacity—and they crash more. So goes the argument up to CC-6.

This line of reasoning requires that there is a "just noticeable difference" between CC-0, CC-1 . . . CC-12. Indeed, the cutoffs were chosen (on the basis of the data) with that in mind. Furthermore, one-dimensional continua such as sound intensity, frequency, and weight are known to fall into 7±2 discretely discriminable categories. With more than nine categories, confusion starts to set in as to which is which. The measure of CC used in this invention proves to have 13 such categories, which is close enough to nine to support the neither fish nor fowl notion. Also, interestingly, CC-0 and CC-12 were the last categories to be added. Their members are rare, fall into the tails of the CC distribution and do not manifest themselves until thousands of people have been given the test. The present invention likely has one of the largest, if not the largest, database of any psychophysical experiment ever run.

In the present test, the path-making task preferably with 15 items per test page is given preferably four times, the last with pictures randomly interspersed among the letters and numbers. The first three pages of the test correspond to the episodic nature of attention, which commonly habituates after three redundant repetitions. Two examples illustrate this point. First, in telling a joke, there are universally three and only three episodes to the set up of the joke, after which the punch line violates the perfectly established expectancy. Two episodes are not enough to establish the point, and more than three episodes is too redundant to maintain the attention of the audience. Second, a magician shows a common object, e.g. a small green ball, three times. Only then is the perfectly established expectancy violated—the ball grows large and blue or perhaps it vanishes.

Analogously, the present invention is structured with three redundant test pages followed by a novel page, measures a person's degree of attention to each redundant set-up episode (based on response rate) and then to the novel punch line episode. SA, then, measures different aspects of attention within the sequence. As such, the five measures of SA are interpreted as follows. SA-1 is viewed as a continuum from a low of slow warm-up (deer in the headlights) to a high of impulsiveness; backing collisions are common to people with slow warm-up. SA-2 is viewed as a general measure of attention in the face of complacency. SA-3 is viewed as a measure of attention in the face of novelty (the first page) relative to attention during distraction/stimulation (the picture page); also short tern attention to the task. SA-4 is viewed as a measure of attention after warm-up relative to attention during distraction/stimulation and also mid-term attention to the task. SA-5 is viewed as a measure of attention after habituation to the task (also complacency) relative to attention during distraction/stimulation and also long-term attention to the task.

If a person has high CC, e.g. above CC-4, he will tend to drive faster. The faster one drives, the more one must be attentive to and remember potential hazards up ahead or in the mirror. Therefore, one would expect SA-5, long term attention, i.e. speed on test page 3 relative to speed on test page 4, to be more predictive of crashes when CC is CCA or above vs. CC-4 and below. Table 1 shows exactly that. At the lower levels of CC, SA-3 (short term attention) and SA-4 (mid term attention) are best for predicting crashes.

Odds ratios, the basis for hiring decisions, are calculated strictly on an empirical basis. Commentary about a person's driving habits is based on a combination of the data and the above theory linking data to theory.

The present invention can be administered in a paper/pencil version, as a computer-based program, and as an Internet or intranet application. The preferred embodiment of the test comprises four pages of 15 numbers and letters (the numbers from 1 to 8 and the letters from A to G) randomly scattered about each page. The fourth page of the test further comprises small images that are neither numbers nor letters interspersed among the numbers and letters. The test can further comprise two additional pages that comprise 12 letters and numbers each, with the second additional page further comprising small pictures interspersed among the numbers and letters. These two additional pages are not used in the scoring, but are used to help prevent subjects from concentrating overly on the actual four pages of the test.

The basic task is to make a continuous path among the numbers and letters, starting at "1" and switching from number to letter, keeping numbers and letters in order (1, A, 2, B, etc.). The subject completes the basic task on all of the pages presented to the subject. For the paper/pencil version, the individual is told to draw the line among the letters and numbers as fast as possible without making mistakes and to keep going if a mistake is made. For the computer-based version, the individual is told to click (using a mouse or other entry device) on the numbers and letters in the alternating order previously mentioned.

The test can be administered to individuals or to groups of people. To administer the test to an individual, the administrator directs the person to the first test page and says, "Pencil on the '1', get set, GO!". A stopwatch is started and then stopped when the person reaches the last point, the "8". This same process is done for all of the test pages presented to the subject. On the test pages with interspersed pictures, the administrator simply says, "Same thing. Forget about the pictures.". The data collected consist of the individual durations, preferably in seconds and tenths of seconds, associated with each of the test pages presented to the subject. Specifically, the data collected is the time it takes for the subject to complete each page of the test. If more than four test pages are presented to the subject (such as in the six pages preferably presented in the paper/pencil version of the test), only the data on the first four test pages is used in the scoring algorithm (a representative algorithm for scoring the test is attached as Appendix 1).

To administer the test to a group of people, the instructions are read and the sample test is taken as with the individual test. The actual test, however, is conducted like a footrace. That is, the administrator tells the group to turn to page 1 and to start "when I say GO!". The first person to get to the "8", the last item, is to yell "STOP!", whereupon everyone must put down their pencil or pen. This procedure is repeated for each of the pages presented to the group. On the pages with interspersed pictures, the administrator says, "Forget about the pictures. Pencil on the "1", etc.", as in the individual test. For each "foot-race" the administrator notes the time of the fastest person.

The test also can be implemented on a computer either as a downloadable program or through a global computer network such as the Internet, or through an intranet. Following is a general example of the computer-based implementation of the test.

Figure 9:
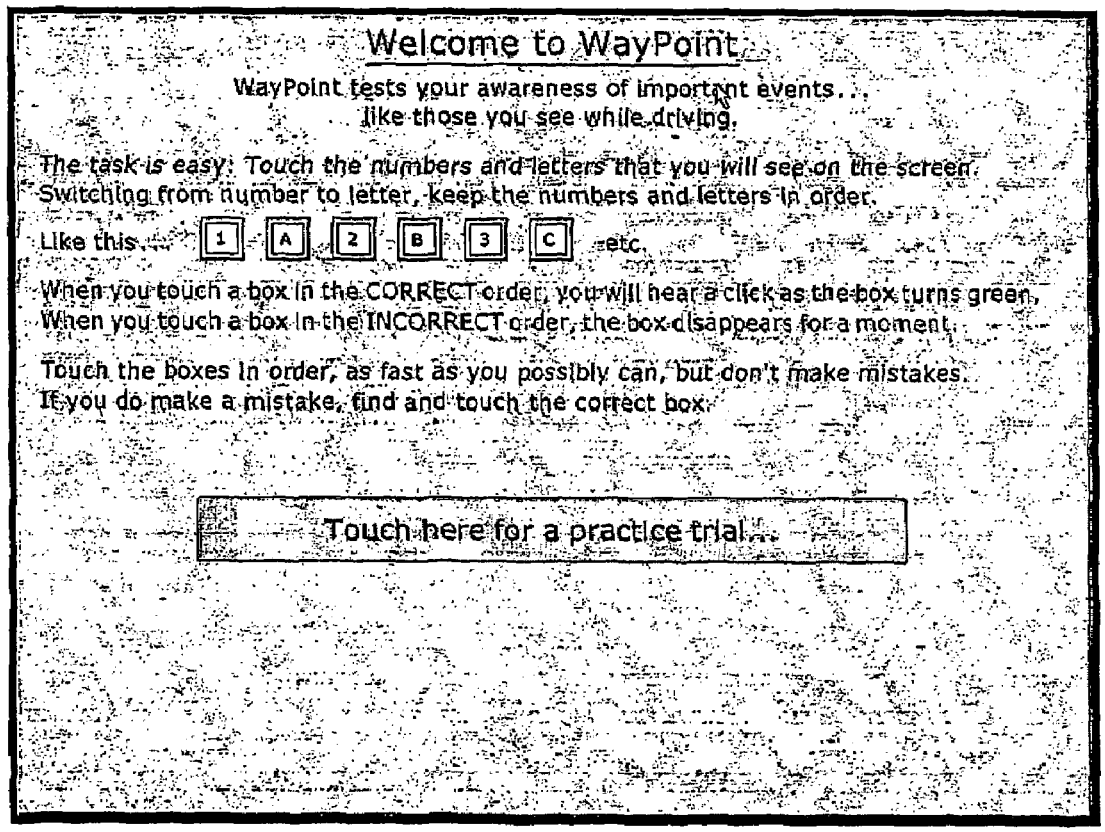
FIG. 9 is a representative opening screen for a computer-based or Internet-based application of the present invention.

The subject accesses the test on the computer. For Internet-based implementations, the subject logs on to the World Wide Web (WWW) and then on to the provider's website. The website can describe the test, offer validations, provide responses to frequently asked questions (FAQs), and offer a test drive, i.e. a static demo of how the test works. The subject can enter a pre-assigned user name and password (or choose a user name and password at that time) and then can be presented with a screen that is tailored to the subject or the subject's company or occupation (e.g. the subject's logo) or to a specific task description (e.g. driver of car, truck, bus, airplane, etc.). The name and other information (bibliographic information) about the subject taking the test can be entered on the next screen. The subject then can be asked to indicate whether the test will be administered on the computer or on paper. If on the computer, a representative opening screen can look like FIG. 9. If on paper, the test pages can be printed out on paper, and the test administered as previously discussed.

For intranet-based implementations, the subject logs on to the company intranet and then on to the test location. As in the Internet implementation, the test location can describe the test, offer validations, provide responses to frequently asked questions (FAQs), and offer a test drive of the test. The name and other information (bibliographic information) about the subject taking the test can be gleaned from the intranet itself, as it is assumed the subject is an employee of the intranet owner. The subject then can be asked to indicate whether the test will be administered on the computer or on paper. If on the computer, a representative opening screen can look like FIG. 9. If on paper, the test pages can be printed out on paper, and the test administered as previously discussed.

For stand-alone computer-based implementations, the subject accesses the testing program (which can be supplied as a download, on diskettes, on CDs or by any other portable media). A description of the test, validations, responses to frequently asked questions (FAQs), and test drives of the test can be included. The name and other information (bibliographic information) about the subject taking the test can be entered, if desired. The subject then can be asked to indicate whether the test will be administered on the computer or on paper. If on the computer, a representative opening screen can look like FIG. 9. If on paper, the test pages can be printed out on paper, and the test administered as previously discussed.

For all electronic-based implementations, the subject preferably then is required to complete at least one practice test and given the choice of doing a second practice test, whereupon the first of four test screens begins. A representative test screen can look like FIG. 10. Following the instructions, the subjects touches (clicks on) the numbers and letters, alternating and in order (1, A, 2, B. etc.). There are three screens like the one shown in FIG. 10, each with a different randomization of numbers and letters. The fourth test screen generally is the same, but it preferably can look like FIG. 11, which contains small figures interspersed among the numbers and letters.

Figure 10:
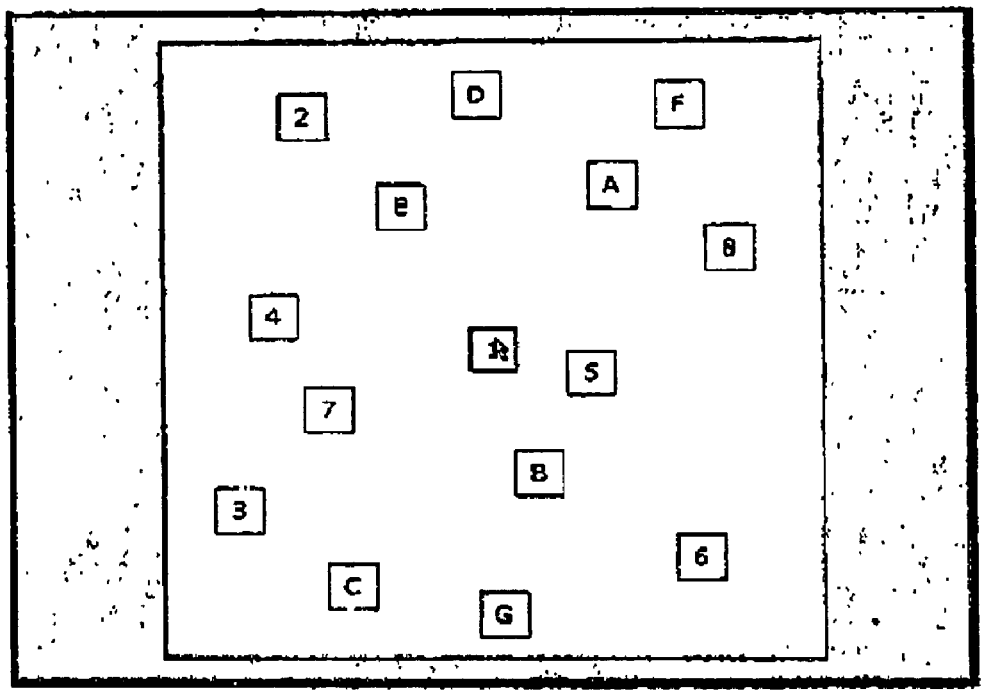
FIG. 10 is a representative sample test screen for the present invention.
Figure 10A:
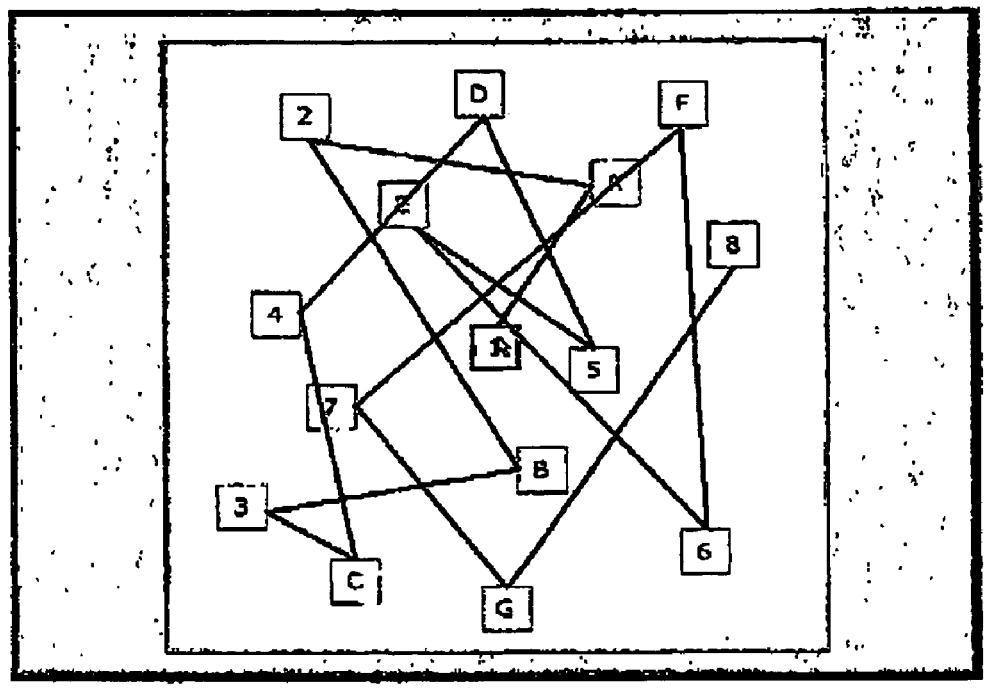
FIG. 10A is the test screen shown In FIG. 10 with the pathway completed.
Figure 11:
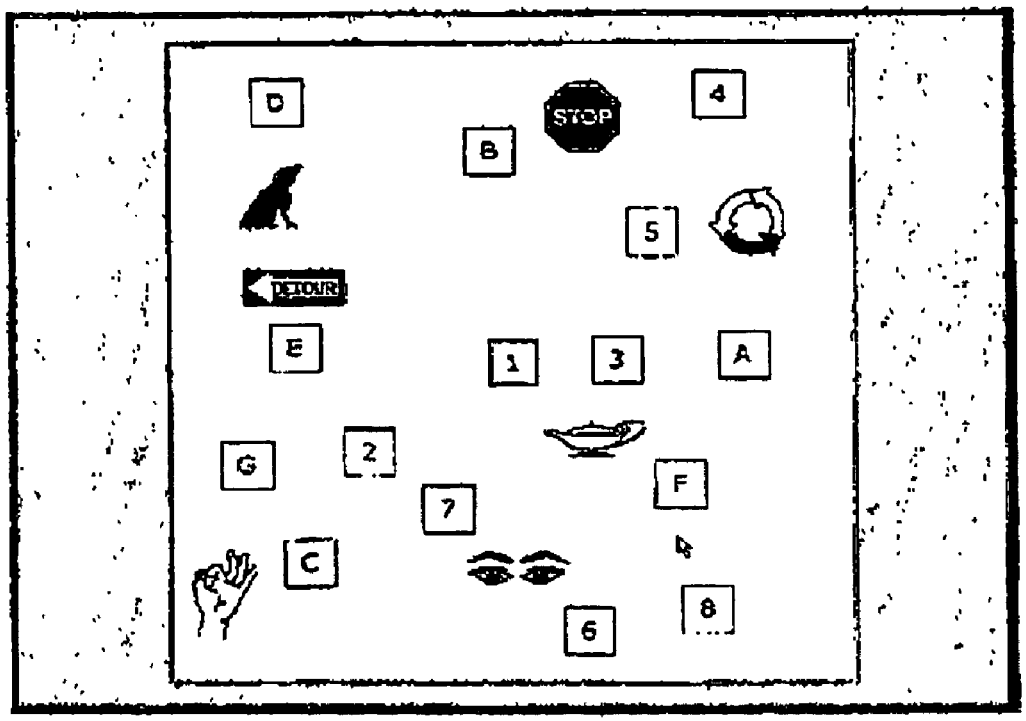
FIG. 11 is a second representative sample test screen for the present invention.
Figure 11A:
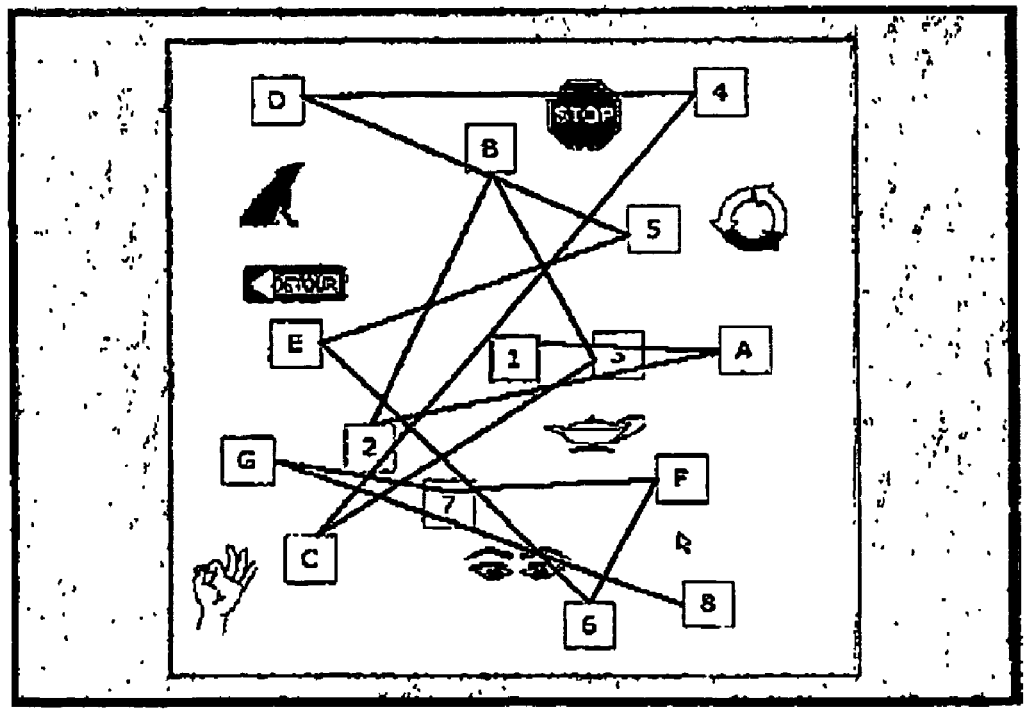
FIG. 11A is the est screen show in FIG. 11 with the pathway completed.

The test is complete when the subject finishes page 4 of the test. FIG. 10A illustrates what FIG. 10 looks like after the subjects touches (clicks on) the numbers and letters, alternating and in order (1, A, 2, B, etc.) on a representative FIG. 10, and FIG. 11A illustrates what FIG. 11 looks like after the subjects touches (clicks on) the numbers and letters, alternating and in order (1, A, 2, B, etc.) on a representative FIG. 11. The algorithm calculates speed on each of the four pages by dividing number of items completed by the time taken to complete them. The program then looks up the mean of test pages 1 and 4 (see Table 1) to determine channel capacity.

Whether administered in individual or group form, the data for each test are "dots"×10 per minute on each page. For the individual test, speed on page n=(15 dots×10)/timePage n. For the group test, speed on page n=(dots traversed×10)/fastest time in the group. So, there is a speed associated with each of the pages presented to the subject or subjects. The scoring algorithm, such as the representative algorithm in Appendix I, is based on two variables derived from the four speeds, channel capacity and situational awareness.

Channel capacity (a communications term that refers to baud rate or bandwidth) is the throughput of a system or, more quantitatively, the amount of information (in bits) that a person can process (as indicated by a response) per unit of time. CC is operationally defined here as the mean speed on test pages 1 and 4. These test pages are used rather than all of the test pages because they have the highest individual correlations with a person's lifetime preventable crash frequency.

Individual differences in CC among people are tremendous. Among 4400 subjects, CC is normally distributed with a mean of 6.004 and a standard deviation of 2.607. Mean CC among 6–7 year-olds is 2.3. It rises to 8.7 by the age of 16–17 and thereafter declines in a linear fashion to a mean of 2.8 among people in their 80's. Between the ages of 16 and 50, there is a substantial (0.4 SD) and statistically significant ($p<0.00001$) difference in CC according to sex. Females are faster.

In scoring the test, CC is divided into 13 class intervals, CC-0 to CC-12, according to empirically determined boundaries. Class intervals for CC were chosen according to 1) homogeneity of variance in crash frequency and 2) so that there was no statistically significant change in crash frequency as a function of mean speed within a bin. The CC upper bounds of the 13 bins are shown in Table 1. Specifically, CC has been divided in to the 13 bins within which preventable crash frequency is unaffected by channel capacity. CC-n is called "CC_bins2" in the algorithm.

Driving speed is directly related to CC. FIG. 1 shows lifetime crash frequency corrected for a driver's age. There is a sharp upturn in crash frequency for drivers with the very slowest CC but overall, preventable crash frequency increases as a function of CC. According to the National Highway Traffic Safety Agency (NHTSA), 36% of male drivers 15 to 20 years old involved in fatal crashes were speeding, whereas only 10% of drivers similarly involved between 45 and 54 were speeding. Given this inverse correlation between age and CC and the inverse relationship between age and driving speed, driving speed and CC are positively correlated. Put another way, people drive at a speed that is commensurate with their ability to process the incoming visual information at that speed. This conclusion fits well with J. S. Wilde's theory of Risk Homeostasis, which states that individuals adjust their behavior so as to hold their personal risk constant.

Situational Awareness (SA) is a measure of a person's relative response rate to certain stimuli. Absolute response speed, CC, is necessary for predicting crash proneness, but it is not sufficient. At each level of CC-n, SA can either aggravate or mitigate the incidence of preventable collisions. Operationally, SA is quantified by five relative response rates (SA-n), i.e. ratios of speed between pages. Specifically, SA-1 is the ratio of the absolute speed (time) it takes the subject to complete test page 1 (S1) to the absolute speed (time) it takes the subject to complete test page 2 (S2), or S1/S2. SA-2 is the ratio of the absolute speed (time) it takes the subject to complete test page 2 (S2) to the absolute speed (time) it takes the subject to complete test page 3 (S3), or S2/S3. SA-3 is the ratio of the absolute speed (time) it takes the subject to complete test page 1 (S1) to the absolute speed (time) it takes the subject to complete test page 4 (S4), or S1/S4. SA-4 is the ratio of the absolute speed (time) it takes the subject to complete test page 2 (S2) to the absolute speed (time) it takes the subject to complete test page 4 (S4), or S2/S4. SA-5 is the ratio of the absolute speed (time) it takes the subject to complete test page 3 (S3) to the absolute speed (time) it takes the subject to complete test page 4 (S4), or S3/S4.

Figure 2:
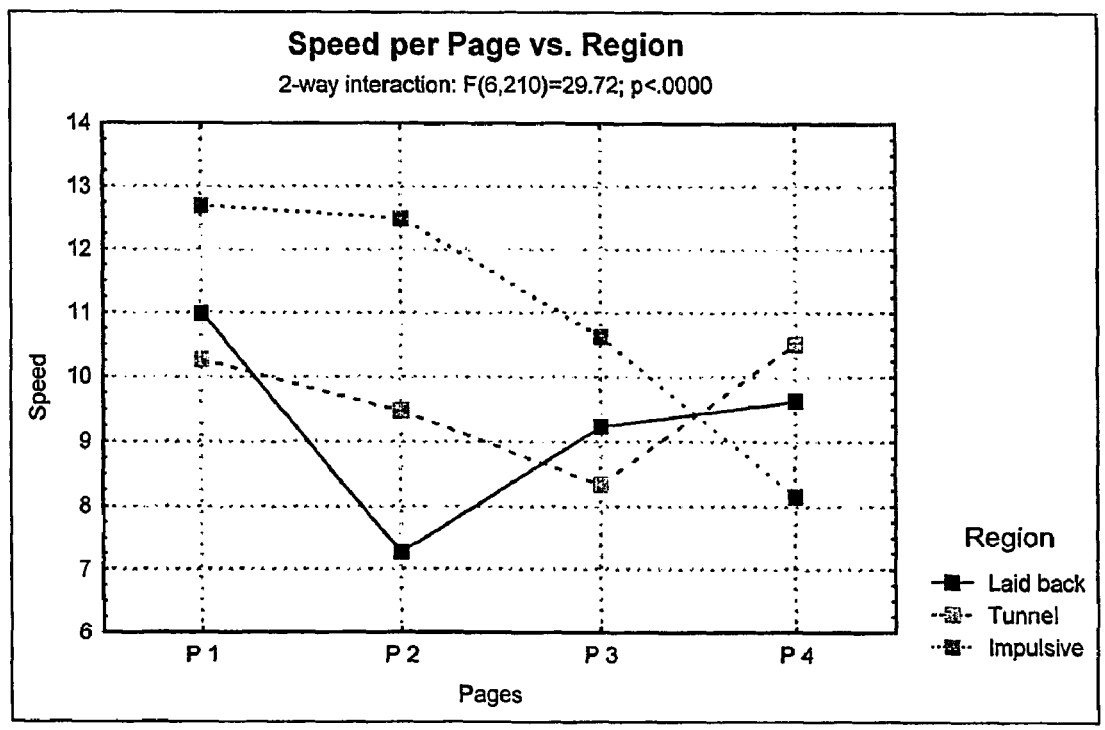
FIG. 2 is a graph of SA-2 versus SA-4 for auto drivers who are CC-10.
Figure 3:
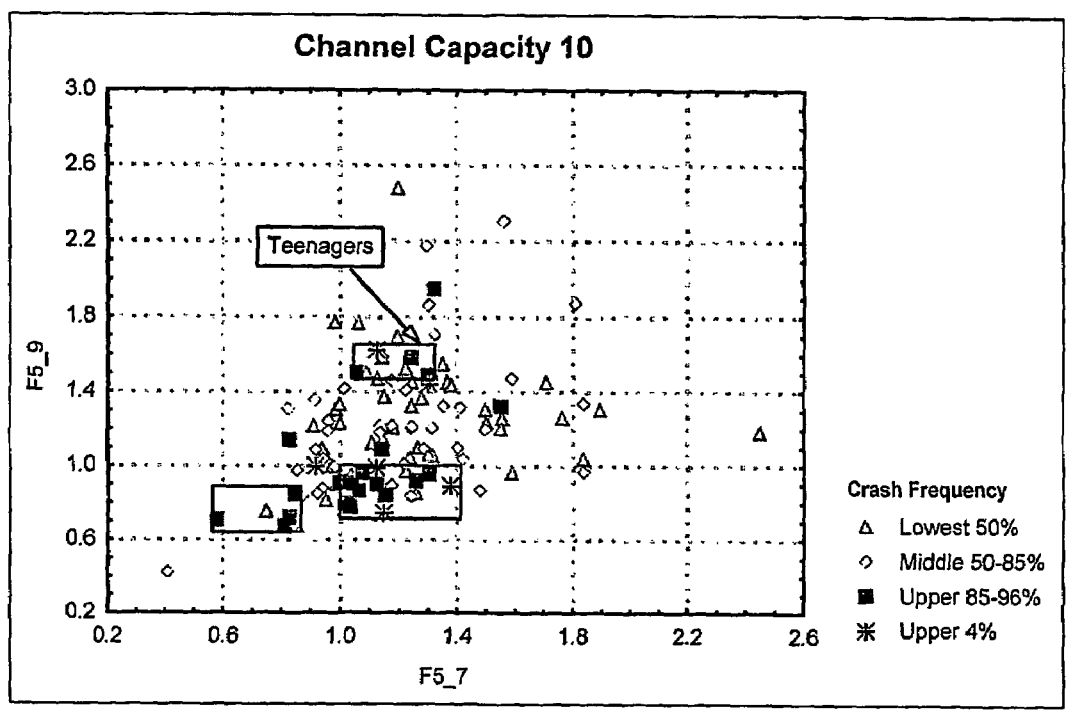
FIG. 3 is a plot of crash frequency for CC-10.

At each level of CC-n, a pair of SA values optimally predicts crash frequency (Table 1). Ratios with X's are the more predictive of the two ratios. As an example, FIG. 2 plots SA-2 against SA-4 for auto drivers who are CC-10. As shown in FIG. 3, the riskiest drivers (upper 15th percentile) cluster in three regions that include relatively few low-risk drivers.

TABLE 1

| CC-n | CC upper bound | SA-1 S1/S2 | SA-2 S2/S3 | SA-3 S1/S4 | SA-4 S2/S4 | SA-5 S3/S4 |
| --- | --- | --- | --- | --- | --- | --- |
| 0 | 1.50 | X | X | | | |
| 1 | 2.20 | | X | | X | |
| 2 | 3.20 | | | | X | X |
| 3 | 4.60 | | X | | X | |
| 4 | 5.80 | | X | | X | |
| 5 | 6.50 | | X | | | X |
| 6 | 7.40 | | | X | | X |
| 7 | 8.00 | | | X | | X |
| 8 | 9.00 | | | | X | X |
| 9 | 9.80 | | | X | X | |
| 10 | 11.40 | | X | | X | |
| 11 | 13.50 | X | | | | X |
| 12 | Hi field | | X | | X | |

Within the lower left rectangle on FIG. 3, the relative frequency of drivers in the upper 15th percentile for crash frequency is 4.7 times that found in the entire database, hence the odds ratio within that region is 4.7. Drivers within this region would be described as laid back, disengaged or lax. The right graph, plotting absolute speed on each page within three regions, shows a striking drop-off in response speed on test page 2 compared to test page 1, hence the "laid back" interpretation. In FIG. 3, the right-most bottom rectangle, drivers are thought to have tunnel vision, i.e. they are riveted to the white line and lack the big picture. The right graph shows that absolute response speed changes little from test page to test page, hence the conclusion that those drivers are tight-focused and switch their attention very little. The odds ratio in that region is 3.5.

Within the upper rectangle on FIG. 3, the odds ratio is 2.8 and the profile can be interpreted as "impulsive". Response rates are high on test pages 1 and 2, fall off on test page 3 and then fall off sharply on test page 4, where the distracting icons (the small interspersed figures) are. It is assumed that a person with this profile would drive similarly, i.e. drive too fast under normal circumstances and be unable to cope with a sudden increase in complexity, as would be the case just before a crash. It is interesting to note that teenagers are over-represented in this region, though more data are needed to support this finding. Outside of the three rectangles, the odds ratio is 1.00, which is average for the entire database.

The relationship between CC and SA, as described in this example, is similar in principal, but not in detail, for each of the 12 other levels of CC. All regions are defined, and odds are shown, in the algorithm attached.

Absolute speed on the test is divided into bins with meaningful boundaries as described above. Relative speed between the pages is used as a measure of response variability that interacts with absolute speed, CC, to predict crash proneness. That particular ratio pairs are maximally predictive of crashes at each level of CC is also unique to this invention. The term "situational awareness" is widely used but the method of operationally defining it is unique to this invention.

The above-disclosed methods are implemented in all versions of the test; paper/pencil (individual), paper/pencil (group test), personal computer-based, and web-based.

Following is a discussion of how the representative exemplary algorithm interprets the data obtained from the test and then scores the test. FIGS. 2 and 3 have been developed for automobile drivers by including information taken from a number of test results, and the following discussion is based on this representative example of automobile drivers. However, the discussion can be extrapolated to other tasks and occupations. For such other tasks, different FIGS. 2 and 3 based on empirical data taken from relevant testing can be loaded into the algorithm.

The algorithm, a series of "If statements" that classify a subject's absolute and relative response speeds on the four test pages, is then applied as follows. For each of the 13 CC-n bins, the algorithm specifies two of the five measures of situational awareness, SA-1, SA-2 . . . SA-5 where each SA-n is a relative response speed. SA-1, for example, is the ratio of speed on page 1 to speed on test page 2. The choice of ratio for a given CC-n is empirically determined. That is, all possible SA's were tried and the two that formed the tightest clusters of high preventable crash drivers (those in the upper 15th percentile corrected for age, i.e. driving exposure) were chosen.

Within a given CC-n, there are several clusters within which preventable crash frequency and/or moving violation frequency (5-year total) is significantly different from the overall rate in the data base. When CC_bin2= (same as CC-0), there are four regions (WP_CAR4) within which high crash drivers cluster. WP_CAR3, for example, is a narrow band within which ratios are close to 1.00. That is, the subject's response rate is constant from page to page; it does not waver. The data show that 75% of the drivers who have this profile are in the upper $15^{th}$ percentile for crash frequency. The odds ratio a subject with that profile is 0.75/0.15=3.4. The chance of being a high risk driver, given that profile, is more than 3 times the chance of the average driver. Further, those drivers have a median of 1 moving violation in 5 years and 3 preventable collisions in 5 years.

The algorithm classifies each person who takes the test in this way. Each man-machine system must have a different algorithm which is empirically determined in a series of validation trials. The long-haul truck algorithm is different from the local delivery truck profile which is different from the airliner profile, etc.

Given CC-n, the algorithm looks up on FIG. 2 which two values of SA are associated with CC-n. Those two SA values for that subject then are looked up in FIG. 3. FIG. 3 shows an example table for CC-5, SA-3 and SA-5. The table in FIG. 3 then defines regions associated with lax, tunnel vision or scattered attention. In addition, the table in FIG. 3 specifies the subject's risk of being in the upper 15th percentile for crash frequency and/or severity in terms of the odds ratio.

A report then is generated based on the person's CC-n and upon the two relevant values of SA associated with it. If, for example, the subject is CC-5 and falls into the region defined by SA-3 and SA-5 as tight focus, then the data show that he can be expected to drive moderately fast, lack the big picture and have rear end or fixed object crashes. In general, CC determines average driving speed and SA determines the way that the person drives from minute to minute.

Figure 8:
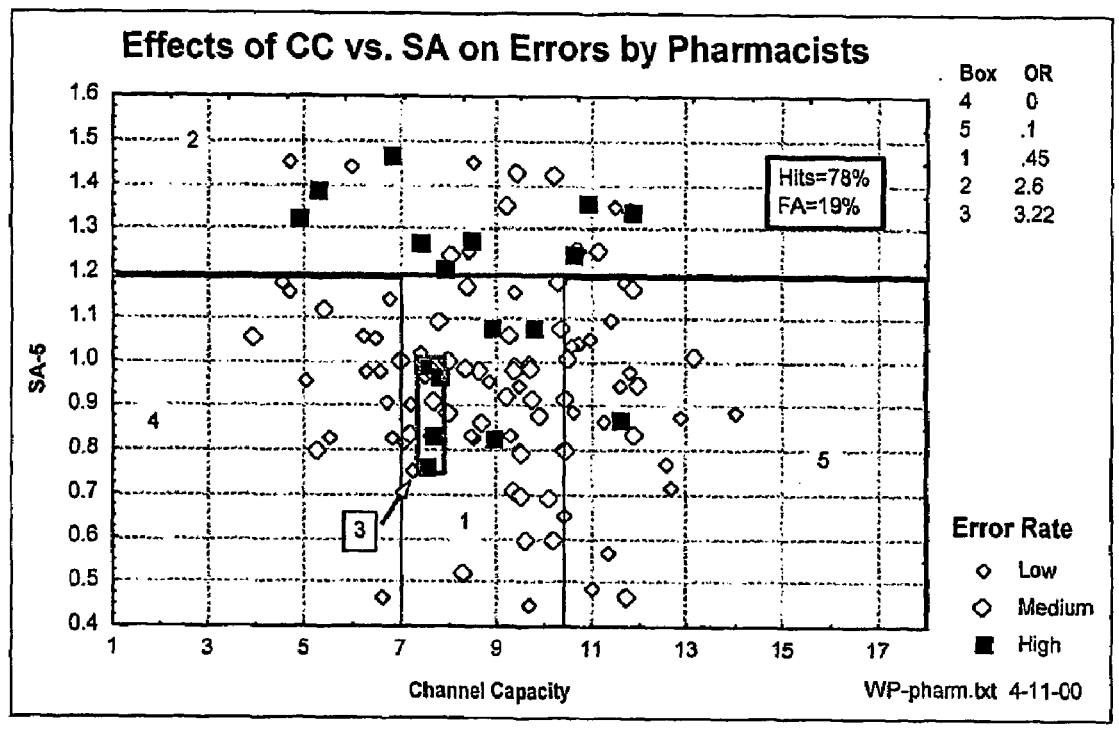
FIG. 8 is a plot of SA-5 versus CC for pharmacists.

Operational tasks other than driving an automobile are scored in the same way. The competence of an airline pilot, for example, is determined by calculating the subject's CC-n and then looking to see where SA-5 falls with respect to FIG. 6. The same is true for pipeline controllers (FIG. 5) and pharmacists (FIG. 8).

The above discussion pertains to automobile drivers. The invention has been validated for other tasks as well. Rather than provide the coordinates for clusters of unsafe or error-prone operators as previously shown for automobiles, in the following examples, an overall scatterplot is presented for each job from which coordinates can be derived.

Figure 4:
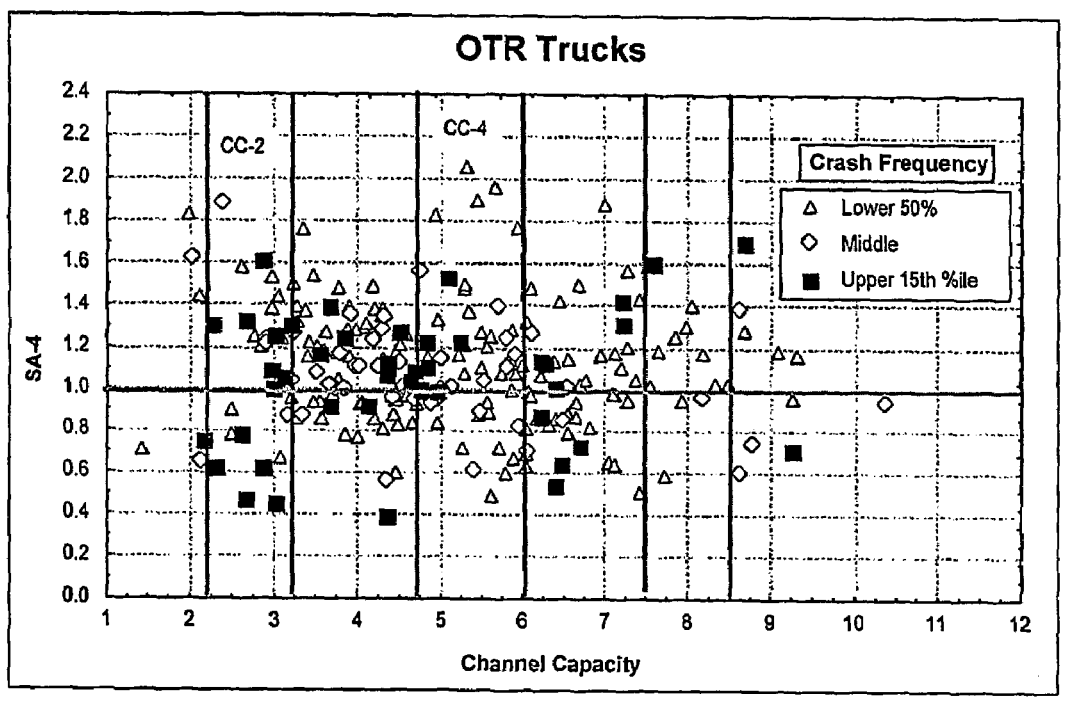
FIG. 4 is a plot of SA-4 versus CC for over the road truck drivers.

The scatterplot in FIG. 4 shows CC (actual, not recoded) on the abscissa and SA-4 on the ordinate for over-the-road (OTR) truck drivers. The filled squares represent drivers in the upper 15th percentile for crash frequency and/or cost. Vertical lines indicate CC-n categories. High Crash drivers, for example, are over-represented among CC-2 drivers and under-represented among CC-4 drivers. As with car drivers, the plot can be used to define profiles of crash-prone over-the-road truck drivers.

Figure 5:
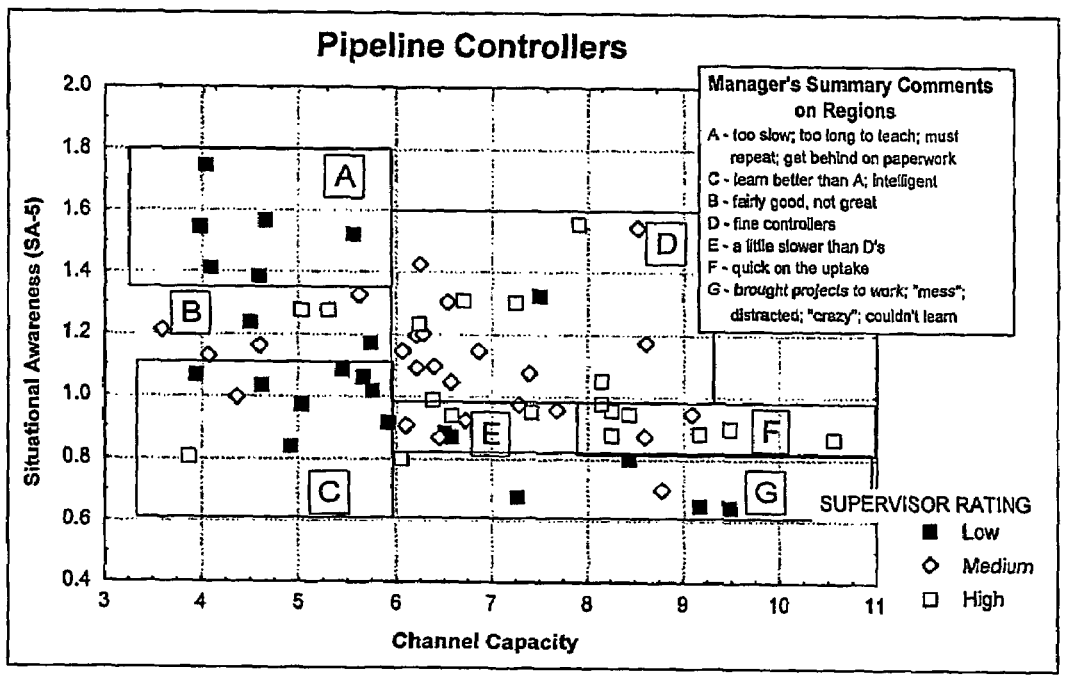
FIG. 5 is a plot of SA-5 versus CC for pipeline controllers.

This test also can be applied to pipeline controllers. The scatterplot in FIG. 5 shows CC (actual, not recoded) on the abscissa and SA-5 on the ordinate. Regions A through G are drawn such that supervisor-defined competence within a region is homogeneous. Every controller whose profile obtained using the present method falls into Region A, for example, received low supervisory ratings. Used as a pre-employment test, then, a candidate's potential for success as a controller is easily assessed.

Figure 6:
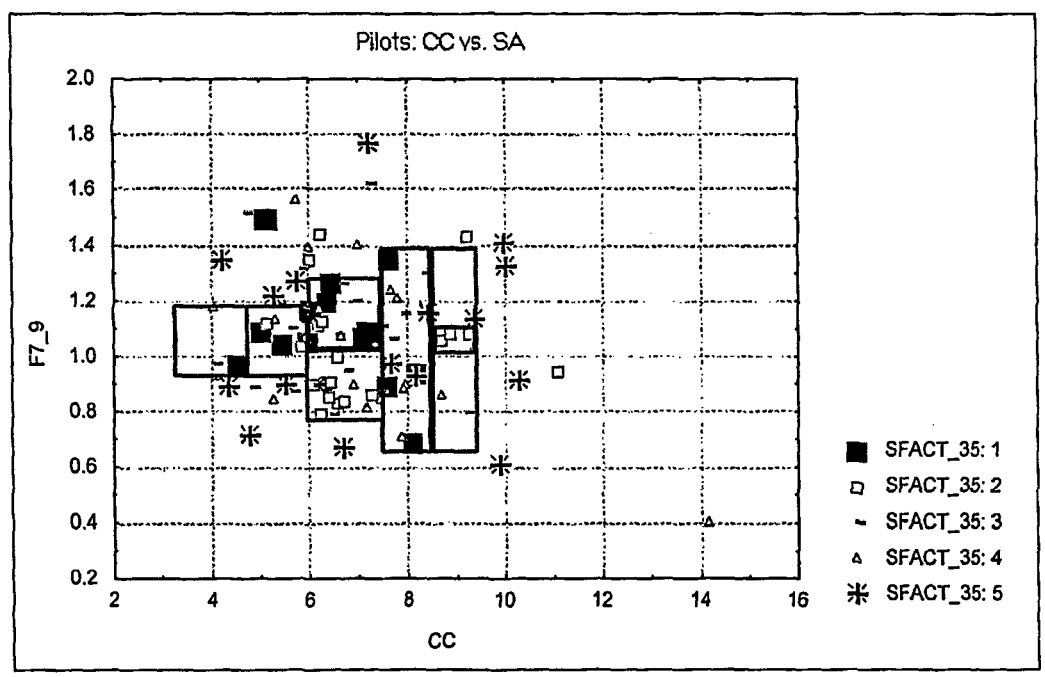
FIG. 6 is a plot of SA versus CC for airline pilots.
Figure 7:
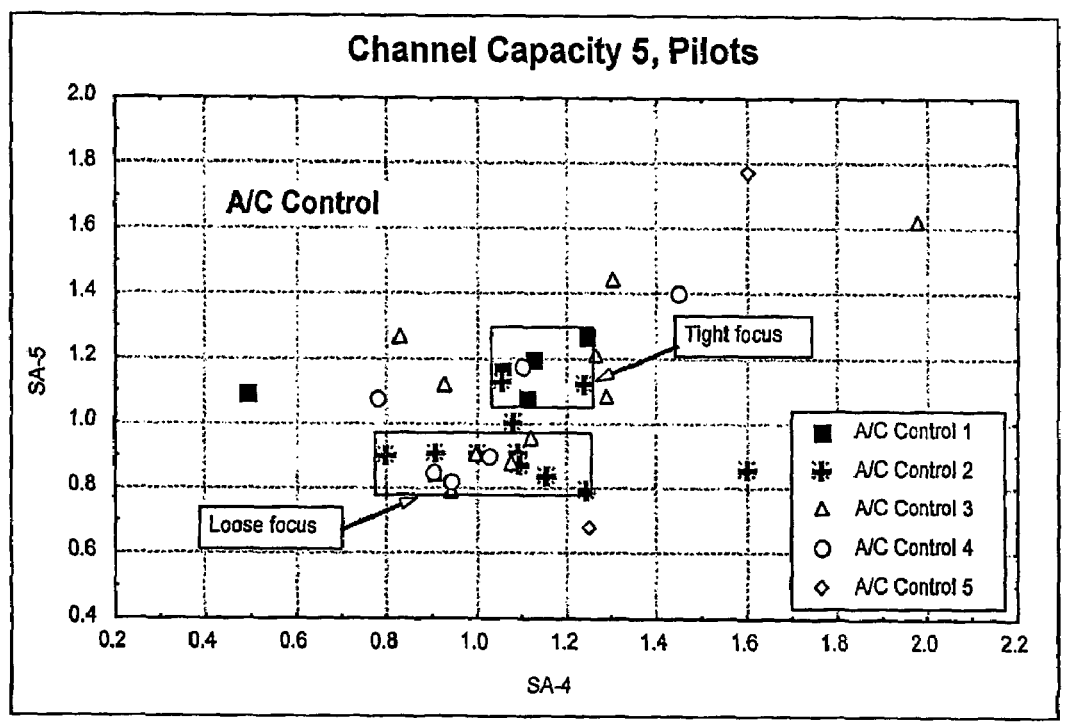
FIG. 7 is a plot of SA-5 versus SA-4 for airline pilots who are CC-5.

This test also can be applied to airline pilots. The scatterplot in FIG. 6 shows data from a validation trial that included 100 airline pilots for whom scores from the test method were compared with check pilot ratings (SFACT_35). Filled squares represent the lowest-rated pilots. As with validations on operators in other man-machine systems, the lowest rated pilots cluster systematically. As shown in FIG. 7, a closer view of only the CC-5 pilots bears this out. Note that the lowest rated pilots cluster within a rectangle centered on approximately 1.2 whereas the second lowest rated pilots cluster in a rectangle centered at SA-4=1.00 and SA-5=0.90. The test is unusual for its ability to make this fine of a discrimination.

This invention also can be applied to pharmacists as a way to predict those who make the greatest number of errors in filling prescriptions. The graph in FIG. 8 shows the results of two studies. Filled squares represent subjects in the validation whose error rate was in the upper 15th percentile. Note the high percentage of error-prone pharmacists with SA-5>1.2 (Region 2). Region 3, within CC-6 and centered at SA-5=0.9 is another high-error region. The odds ratio of errors is shown in the upper right corner of the graph, e.g. Region 2, has an odds ratio of 2.6. These data are the basis for using this invention as a pre-employment test for pharmacists.

Although the present invention has been described with reference to preferred embodiments and relative examples thereof, it is to be understood that these embodiments are for illustrative purposes and should not be construed as limitations on the scope of the invention. Accordingly, the spirit and scope of the present invention should not be determined by the embodiments illustrated, but by the claims appended hereto and their legal equivalents.

| Variable | Definition |
| --- | --- |
| CC_BINS2 | Class intervals of channel capacity; 0–12 |
| F3_5 | Ratio of speed Page1:Page2 |
| F5_7 | Ratio of speed Page2:Page3 |
| F3_9 | Ratio of speed Page1:Page4 |
| F5_9 | Ratio of speed Page2:Page4 |
| F7_9 | Ratio of speed Page3:Page4 |
| WP_CAR4 | Critical SA1 x SA 2 regions within each CC_BINS2 |
| ORP | Odds ratio, lifetime preventable collisions |
| P6M | Median 5-year preventable collisions |
| ORTKT | Odds ratio, tickets 5 years |
| TKTM | Median 5-year tickets |

What is claimed is:

1. A method of testing competence for operating machines, comprising the steps of:
    a) successively presenting a plurality of pages of randomly scattered images to a subject;
    b) having the subject establish a path through the randomly scattered images on each of the plurality of pages;
    c) recording an absolute time required for the subject to establish the path through the randomly scattered images on each of the plurality of pages;
    d) determining a relative time required for the subject to establish the path on at least two of the plurality of pages of randomly scattered images; and
    e) classifying the competence of the subject for operating machines based on the absolute time and the relative time, wherein the combination of the absolute time and the relative time correlate with the competence for operating machines.

2. The method as claimed in claim 1, wherein the randomly scattered images comprise letters and numbers.

3. The method as claimed in claim 2, wherein the letters are consecutive letters.

4. The method as claimed in claim 3, wherein the consecutive letters start with A.

5. The method as claimed in claim 3, wherein the letters are seven consecutive letters.

6. The method as claimed in claim 5, wherein the seven consecutive letters are A through G.

7. The method as claimed in claim 2, wherein the numbers are consecutive numbers.

8. The method as claimed in claim 7, wherein the consecutive numbers start with 1.

9. The method as claimed in claim 7, wherein the consecutive numbers are eight consecutive numbers.

10. The method as claimed in claim 9, wherein the eight consecutive numbers are 1 through 8.

11. The method as claimed in claim 2, wherein the plurality of pages consists four pages; and each of the four pages comprises randomly scattered letters and numbers.

12. The method as claimed in claim 11, wherein the plurality of pages consists of four pages; and one of the four pages of comprises randomly scattered letters and numbers further comprises additional images that are neither letters nor numbers.

13. The method as claimed in claim 2, wherein the path is determined through the randomly scattered letters and numbers by alternating between numbers and letters.

14. The method as claimed in claim 2, wherein the letters are consecutive letters and the numbers are consecutive numbers, and the path is predetermined through the letters and numbers by alternating between numbers and letters starting with the lowest number and the alphabetically first letter.

15. The method as claimed in claim 1 wherein the plurality of pages consists of four pages; and each of the four pages comprises randomly scattered images.

16. The method as claimed in claim 1, wherein the path through the randomly scattered images is predetermined.

17. The method as claimed in claim 1, wherein the absolute time to complete each path is compared with the relative time to complete at least two of the paths to arrive at a competence level.

18. The method as claimed in claim 17, wherein the competence level classifies the subject's relative competence level for operating a machine.

19. The method as claimed in claim 17, wherein the competence level classifies the subject's relative competence to perform a task.

20. The method as claimed in claim 17, wherein the competence level classifies the subject's relative competence to perform an occupation.

21. A method of testing competence for operating machines, comprising the steps of:
  a) successively presenting a plurality of pages of randomly scattered consecutive letters and consecutive numbers to a subject;
  b) having the subject establish a predetermined path through the randomly scattered images on each of the plurality of pages by selecting between alternating numbers and letters starting with the lowest number and the alphabetically first letter;
  c) recording an absolute time required for the subject to establish the path through the randomly scattered images on each of the plurality of pages;
  d) determining a relative time required for the subject to establish the path on at least two of the plurality of pages of randomly scattered images; and
  e) classifying the competence of the subject for operating machines based on the absolute time and the relative time, wherein the combination of the absolute time and the relative time correlate with the competence for operating machines.

22. The method as claimed in claim 21, wherein the consecutive letters start with A and the consecutive numbers start with the 1.

23. The method as claimed in claim 22, wherein the consecutive letters are the seven consecutive letters from A through G and the consecutive numbers are the eight consecutive numbers from 1 through 8.

24. The method as claimed in claim 23, wherein the plurality of pages consists of four pages; and the four pages consist of randomly scattered letters and numbers.

25. The method as claimed in claim 24, wherein one page further comprises additional images that are neither letters nor numbers.

26. The method as claimed in claim 25, wherein the absolute time to complete each path is compared with the relative time to complete at least two of the paths to arrive at a competence level.

27. The method as claimed in claim 26, wherein the competence level classified is classified as the subject's relative competence level for operating a machine.

28. The method as claimed in claim 26, wherein the competence level classifies the subject's relative competence to perform a task.

29. The method as claimed in claim 26, wherein the competence level classifies the subject's relative competence to perform an occupation.

30. A method of testing competence for operating machines, comprising the steps of:
  a) successively presenting a plurality of pages of scattered images to a subject;
  b) having the subject establish a path through the scattered images on each of the plurality of pages;
  c) recording the absolute time required for the subject to establish the path through the scattered images on each of the plurality of pages;
  d) determining the relative time required for the subject to establish the path on at least two of the plurality of pages of scattered images; and
  e) classifying the competence of the subject for operating machines based on the absolute time and the relative time, wherein the combination of the absolute time and the relative time correlate with the competence for operating machines.

31. The method as claimed in claim 30, wherein the randomly scattered images comprise letters and numbers.

32. The method as claimed in claim 31, wherein the letters are consecutive letters and the numbers are consecutive numbers.

33. The method as claimed in claim 32, wherein the consecutive letters start with A and the consecutive numbers start with 1.

34. The method as claimed in claim 33, wherein the consecutive letters are the seven consecutive letters from A through G and the consecutive numbers are the eight consecutive numbers from 1 through 8.

35. The method as claimed in claim 34, wherein the plurality of pages consists of four pages; and the four pages consist of scattered letters and numbers.

36. The method as claimed in claim 35, wherein one of the four pages further comprises additional images that are neither letters nor numbers.

37. The method as claimed in claim 36, wherein the subject establishes a predetermined path through the scattered images.

38. The method as claimed in claim 37, wherein the path of each page is predetermined and the subject establishes the predetermined path through the scattered letters and numbers by selecting alternating between numbers and letters.

39. The method as claimed in claim 38, wherein the path of each page is predetermined and the subject establishes the path through the scattered letters and numbers by selecting alternating between numbers and letters starting with the lowest number and the alphabetically first letter.

40. The method as claimed in claim 39, wherein the absolute time to complete each path is compared with the relative time to complete at least two of the paths to arrive at a competence level.

41. The method as claimed in claim 40, wherein the scattered images are randomly scattered on at least one page.

42. The method as claimed in claim 41, wherein the competence level classifies the subject's relative competence level for operating a machine.

43. The method as claimed in claim 42, wherein the competence level classifies the subject's relative competence to perform a task.

44. The method as claimed in claim 43, wherein the competence level is classifies the subject's relative competence to perform an occupation.

45. A method of testing a subject's competence for operating machines, comprising the steps of:
 a) successively presenting a plurality of pages of randomly scattered consecutive letters and consecutive numbers to a subject, wherein the consecutive letters are the seven consecutive letters from A through G and the consecutive numbers are the eight consecutive numbers from 1 through 8;
 b) having the subject establish a predetermined path through the randomly scattered images on each of the plurality of pages by selecting between alternating numbers and letters starting with the lowest number and the alphabetically first letter;
 c) recording an absolute time required for the subject to establish the path through the randomly scattered images on each of the plurality of pages;
 d) determining an relative time required for the subject to establish the path on at least two of the plurality of pages of randomly scattered images; and
 e) classifying the competence of the subject for operating machines based on the absolute time and the relative time, wherein the combination of the absolute time and the relative time correlate with the competence for operating machines.

46. The method as claimed in claim 45, wherein the plurality of pages consists of four pages, and wherein one of the four pages further comprises additional images that are neither letters nor numbers.

47. The method as claimed in claim 46, wherein the absolute time to complete each path is compared with the relative time to complete at least two of the paths to arrive at a competence level.

48. The method as claimed in claim 47, wherein the competence level classifies the subject's relative competence level for operating a machine.

49. The method as claimed in claim 47, wherein the competence level classifies the subject's relative competence to perform a task.

50. The method as claimed in claim 47, wherein the competence level classifies the subject's relative competence to perform an occupation.

51. The method as claimed in claim 46, wherein the subject is given a maximum of four minutes to complete the paths through each of the pages.

* * * * *